United States Patent [19]

Lyons et al.

[11] 4,190,611
[45] Feb. 26, 1980

[54] CATALYTIC CODIMERIZATION OF NORBORNADIENE WITH NORBORNENE

[75] Inventors: James E. Lyons, Wallingford; Harry K. Myers, Jr., Aston; Abraham Schneider, Overbrook Hills, all of Pa.

[73] Assignee: Sun Oil Company of Pennsylvania, Philadelphia, Pa.

[21] Appl. No.: 933,230

[22] Filed: Aug. 14, 1978

Related U.S. Application Data

[63] Continuation of Ser. No. 819,442, Jul. 27, 1977, abandoned.

[51] Int. Cl.$^2$ ............................................. C07C 13/32
[52] U.S. Cl. .................................... 585/361; 585/14; 585/22; 149/120
[58] Field of Search ......... 260/666 A, 666 B, 666 PY

[56] References Cited

U.S. PATENT DOCUMENTS 2,875,256  2/1959  Hyman ........................... 260/666 A

OTHER PUBLICATIONS

Carbonaro, J. Org. Chem., 36, p. 1443, 1971.
Mitsudo et al., J. Chem. Soc. Chem. Com., pp. 772-773, 1976.
Hara et al., Tetrahedron, 22, pp. 95-100, 1966.
Cagill et al., J. Org. Chem., 31, p. 3938, 1966.
Greco et al., J. Org. Chem., 35, p. 271, 1970.

*Primary Examiner*—Veronica O'Keefe
*Attorney, Agent, or Firm*—J. Edward Hess; Donald R. Johnson; Anthony Potts, Jr.

[57] ABSTRACT

Norbornadiene and nobornene are catalytically codimerized to the saturated exo-exo hexacyclic dimer of norbornadiene. Used is a three-component homogeneous catalytic system consisting of cobaltic or cobaltous acetylacetonate, 1,2-bisdiphenylphosphino ethane and an alkyl aluminum chloride. Resulting dimer can be used as a component of high energy fuel.

10 Claims, No Drawings

CATALYTIC CODIMERIZATION OF NORBORNADIENE WITH NORBORNENE

The invention herein described was made in the course of or under a contract thereunder with the United States Air Force Systems Command.

This is a continuation of application Ser. No. 819,442, filed July 27, 1977, now abandoned.

BACKGROUND OF THE INVENTION

The invention relates to the catalytic codimerization of norbornadiene and norbornene. Particularly the invention relates to the preparation of a codimer of norbornadiene and norbornene using a specified catalyst system. The resulting saturated codimer has utility as a component of high energy fuel. The norbornene hereinafter shall be referred to as NB.

High energy fuel, which is often referred to as a high density fuel, can be used in either jet or rocket propulsion. Jet propulsion includes a jet engine which can be used for a missile plane and others and includes the three basic types, i.e., ramjet, turbo-jet and pulse jet. The term rocket generally refers to a device containing its own oxygen or oxidizing agent.

Norbornadiene is also known as bicyclo-(2.2.1) heptadiene-2,5. A method of preparation is disclosed in U.S. Pat. No. 2,875,256 issued Feb. 24, 1959. Hereinafter, norbornadiene is referred to as NBD. The latter can be represented by either one of the following structural formulas:

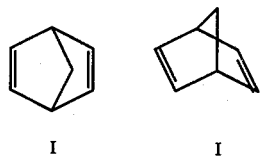

I      I

NB is also known as bicyclo-(2.2.1) heptene-2. It can be prepared by reacting dicyopentadiene with ethylene at 200° C. and 800 psi. The NB can be represented by either on of the following structural formulas:

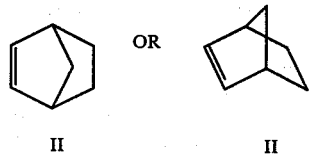

II      II

NBD by itself will homodimerize to form an olefinic exo-exo hexacyclic dimer. Because of its olefinic nature the exo-exo hexacyclic dimer has a tendency to form gums and other like undesirable materials. The formation of such materials makes it undesirable as a fuel and to overcome the olefinic dimer is hydrogentated. The hydrogenated product is then useful as a component of high energy fuel.

A one step method with its advantages of reduced investments and operating costs for making the saturated exo-exo hexacyclic dimer of norbornadiene is desirable.

SUMMARY OF THE INVENTION

Codimerization of NBD and NB is obtained using a catalytic amount of a three-component homogeneous catalytic system consisting of cobaltic or cobaltous acetylacetonate 1,2-bisdiphenylphosphino ethane and one of three alkyl aluminum chlorides. Resulting saturated codimer can be used as a component of a missile fuel.

DESCRIPTION

Cobaltic acetylacetonate ($Co(C_5H_7O_2)_3$) is referred to hereinafter as $CoA_3$ whereas the cobaltus form ($Co(C_5H_7O_2)_2$) is referred to as $CoA_2$. Collectively the two are referred to as CoA. The 1,2-bidiphenylphosphino ethane is referred to as DIPHOS while alkyl aluminum chloride is referred to as AAC.

The catalytic codimerization of NBD and NB via present invention can be represented by the following formula reaction:

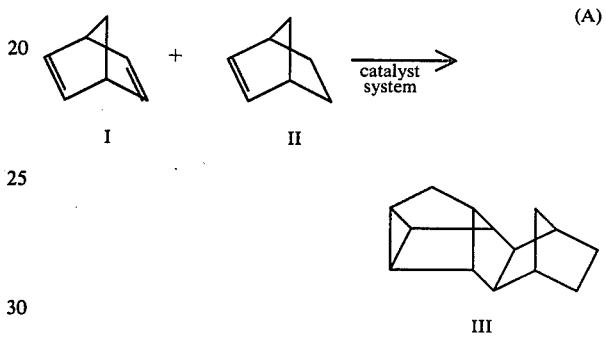

Coproducts may also be formed. As shown NBD and NB are contacted in the presence of a catalytic amount of the catalyst system defined herein.

Saturated codimer III, is identical to the hydrogenated exo-exo hexacyclic homo dimer of NBD. Codimer III, prepared as described hereinafter, with a purity of 88%, has a net heating value of 158,883 BTU/gal., a density of 1.0675 (20°C. /4) a KV @100°F. of 13.5 cs. It has a formula of $C_{14}H_{18}$, a C/H molar ratio of 0.779 and contains 6 rings.

The NBD used can contain a nominal amount of similar hydrocarbons, however, which if present should not be of the type which could adversely effect the reaction. If the NBD used contains undesirable hydrocarbons, they can be removed by known means. The foregoing also applies to the NB used. Thus the hydrocarbons used in the invention can consist essentially of NBD and NB.

In the codimerization of NBD and NB one mole of each reacts with the other to form one mole of the NBD-NB codimer II. However, if the NBD to NB mole ratio is too large homodimerization can occur with an adverse effect on codimer yields. On the other hand, if the NBD to NB mole ratio is too low then the yield per pass can be too low and hence uneconomical. Within the aforementioned limits a preferred NBD to NB mole ratio is in the range between from about 0.1 to about 20 with about 0.2 to about 10 more preferred.

The catalytic system favoring the aforementioned codimerization reaction (A) contains three components. All three components of the catalyst system are commercially available and methods for their preparation are reported in the literature. The three are $CoA_3$ or $CoA_2$, DIPHOS and AAC. The AAC can be selected from the group consisting of diethylaluminum chloride, ethyl aluminum dichloride and ethyl aluminum sesquichloride. The latter three are referred to as DEAC, EADC and EASC, respectively. The amount of any component present is a catalytic amount so that a suitable conversion to codimer II occurs and the selectivity as to it is sufficient. Material, which during the codimerization reaction could adversely effect the catalyst system, should not be present. For example, the presence of hydroxylic compounds such as water, alcohol or oxygen from air could deactivate the catalyst system.

The amount of CoA present should be catalytically sufficient to obtain the desired product. Generally the NBD to CoA mole ratio can range between from about 10 to about 2000 with a preferred range between from about 20 to about 1000.

The second component of the catalyst system is DIPHOS. The amount of this second component of the catalyst system should be catalytically sufficient to obtain the desired product. Generally the DIPHOS to CoA mole ratio can range between from about 0.1 to about 5, with a preferred range between from about 0.25 to about 3.

DEAC, EADC or EASC is the third component of the catalyst system with DEAC preferred. The amount of the third component can vary substantially but generally it relates to the amount of CoA used. An effective DEAC, EADC or EASC to CoA mole ratio can be between from about 0.5 to about 100 with from about 1 to about 50 preferred and from about 3 to about 20 more preferred. Generally, when DEAC, EADC or EASC is used it is advantageous to conduct the reaction under substantially anhydrous conditions and under an inert gas blanket. Excess DEAC, EADC or EASC also serves as a scavenger.

Selectivity refers to the amount, mole or weight, of a particular compound formed divided by the amount of all compounds formed. From a commercial standpoint the economics of an overall process determines the optimal levels for both the selectivity and yield.

The reaction time required for an economically satisfactory selectivity and/or yield depends on a number of factors, such as catalyst to feed ratio, as well as operating conditions. Also the economics depend on capital investment versus conversion per pass and the like. The catalyst to feed ratios are discussed herein while typical conditions are provided by the Example.

A solvent can be used in the codimerization reaction. The solvent can be inert or it can be the NBD itself. Since the reaction is mildly exothermic the solvent can serve as a heat sink. It can also assist in solubilizing the reaction components, that is the feed and the components of the catalyst, and thereby provide for a homogeneous reaction medium. Some solvent can be added to the system as a carrier for one or more of the catalyst components. For example, DEAC is often maintained in an inert solvent such as toluene rather than NBD itself. Furthermore, the solvent should not adversely react with the feed, products or catalyst, therefore, if it is not NBD, it should be inert. Also, presence of the solvent can facilitate the handling of the reaction mixture. Classes of suitable inert solvents include aromatic hydrocarbons, cycloparaffins, ethers, halogenated aromatics, halogenated paraffins and halogenated cycloparaffins. Specific examples include benzene, toluene, xylenes, cyclohexane, cyclopentane, diethylether, chlorobenzene, bromobenzene, chlorinated cyclohexane and the like. As to the amount of solvent used, excessive amounts decrease the reaction rate, and thus adversely affect the economics for a commercial operation.

The codimerization of NBD and NB with the three-component catalyst system can occur at ambient temperature. Thus the temperature of the homogeneous feed catalyst system mixture need not be raised to initiate reaction A. However, if the mixture is at an extremely low temperature, then heating of the cooled mixture could be necessary. Furthermore, once reaction A is underway, some heat is generated and the temperature of the mixture increases. If the temperature increases too much then some cooling would be required. Generally, however, the codimerization of NBD and NB with a reasonable amount of the three-component catalyst system is not characterized by an extremely rapid exotherm.

Selective codimerization of the NBD and NB most efficiently occurs in a liquid phase and therefore it is not desirable to have the reaction temperature largely exceed the boiling points of the NBD and/or any solvent. Conversely, if the temperature is too low the reacction rate will be too slow to be economically feasible. An operable temperature range is between from about 20° C. to about 100° C. with about 40° C. to about 70° C. a preferred range. The operating pressure can vary substantially, however, it can range from about atmospheric up to about 2000 psi with about 1000 psi a preferred upper value. Process economics favor lower operating pressure.

To further illustrate the invention the following examples are provided.

EXAMPLES

The accompanying Table I summarizes the codimerization runs which were performed. Runs 1, 2 and 3 were screening runs and the results are of a qualitative nature. Run 4 was a larger scale controlled reaction from which the codimer was isolated and identified.

The following description is directed to run 4 because from this run the codimer was isolated. The procedure used in run 4 was generally followed for runs 1–3. Smaller amounts of materials were used in run 1–3 compared to the run 4. Also runs 1–3 were conducted in test tubes.

Into a glass pressure vessel were placed 0.356 grams (1 millimole) of $CoA_3$; 0.597 grams (1.5 millimoles) of DIPHOS, 15 milliliters of toluene, 1 milliliter of NBD and 5 grams of NB. The resulting mixture was deaerated and then chilled to $-10°$ C. A second glass pressure vessel was charged with 10.5 milliliters of NBD, 10 milliliters of toluene and 27.43 grams of NB. Then 15 milliliters of a 1 molar solution of DEAC were added to the first vessel and within 20 seconds the temperature rose 1° C. At this point the mixture of the second vessel were pumped slowly into the first vessel. An exothermic reaction occured which caused the temperature to rise to 51° C. in 27 minutes.

The exothermic reaction mixture was then cooled to about 35° C. and held at that lower temperature for about 100 minutes. Then the mixture was at about 40°–60° C. for about 15 minutes at which time the mixture was quenched with aqueous HCl to kill the catalyst. The quenched mixture was filtered and then distilled. A distilled cut, 3.5 grams, boiling at about 94° C. at about 0.5 mm of Hg, contained 54% codimer and 45% exo-exo-hexacyclic NBD dimer. The codimer was separated from the dimer by vapor phase chromatography. The codimer was shown to be identical to the hydrogenated exo-exo hexacyclic NBD dimer by vapor phase chromatography, mass spectrometry, infrared analysis and nuclear magnetic resonance.

TABLE I

CODIMERIZATION OF NBD AND NB CONDITIONS[b] and RESULTS

| Runs | Amounts (gms)[a] | | | | | Time min. | Conversion of monomer wt. % | Yield of Dimer wt. % | Selectivity % | |
|---|---|---|---|---|---|---|---|---|---|---|
| | CoA$_3$ | DIPHOS | DEAC | NBD | NB | | | | Exo-Exo Codimer | Exo-Exo Dimer |
| 1 | 0.0066 | 0.0082 | 0.037 | 0.90 | 9.50 | 220 | 16 | 15 | 3.0 | 19.3 |
| 2 | 0.0075 | 0.0107 | 0.037 | 0.90 | 1.0 | .334 | 12 | 11 | 7.8 | 22.4 |
| 3 | 0.0061 | 0.0086 | 0.037 | 0.45 | 1.0 | 220 | 3[c] | 3[c] | 28.0 | 6.4 |
| 4 | 0.356 | 0.597 | 1.80 | 10.6 | 32.4 | 140 | 9 | 8 | 42.0 | 44.0 |

Notes
[a]In addition, in Runs 1–3 some 0.040 ml. of toluene were used while in Run 4 some 33.0 gms were used.
[b]Maximum temperature for all runs was 60° C.
[c]In run 3 for some unexplained reason the catalyst apparently died rather quickly.

The following Table II which lists the codimer yield from Runs 1–4 along with NBD/NB weight ratio, suggest that as the NBD/NB ratio decreases the selectivity as to codimer increases.

TABLE II

| NBD/NB Ratio | Codimer Selectivity Weight % |
|---|---|
| 1.8 | 3.0 |
| 0.9 | 7.8 |
| 0.45 | 28.0 |
| 0.33 | 42.0 |

Analogous results will be obtained when CoA$_2$ is used in lieu of CoA$_3$. Also similar results will be obtained if DEAC is replaced by either EADC or EASC.

The invention claimed is:

1. Process for the catalytic codimerization of norbornadiene and norbornene comprising:
   (a) contacting norbornadiene and norbornene in the presence of a catalytic amount of a three-component homogeneous catalytic system consisting of cobaltic or cobaltous acetylacetonate, 1,2-bisdiphenylphosphino ethane and one of the following alkyl aluminum chlorides: diethylaluminum chloride, ethyl aluminum dichloride and ethyl aluminum sesquichloride;
   (b) having the contacting occurring at a temperature within the range from between about 20° C. to about 100° C.; and
   (c) continuing the contacting until the codimer of norbornadiene and norbornene is prepared.

2. Process according to claim 1 wherein the bisdiphenylphosphino ethane to the acetylacetonate mole ratio is in the range between from about 0.1 to about 5.

3. Process according to claim 1 wherein the norbornadiene to the norbornene mole ratio is in the range between from about 0.1 to about 20.

4. Process according to claim 1 wherein the alkyl aluminum chloride to the acetylacetonate mole ratio is in the range between from about 0.5 to about 100.

5. Process according to claim 1 wherein the norbornadiene to the acetylacetonate mole ratio is in the range between from about 10 to about 2000.

6. Process according to claim 5 wherein an inert solvent is present.

7. Process according to claim 6 wherein the inert solvent is selected from the group consisting of aromatic hydrocarbon, cycloparaffin, ether, halogenated aromatic hydrocarbon, halogenated paraffin and halogenated cycloparaffin.

8. Process according to claim 7 wherein the bisdiphenylphosphino ethane to the acetylacetonate mole ratio is in the range between from about 0.1 to about 5.

9. Process according to claim 8 wherein the norbornadiene to the norbornene mole ratio is in the range between from about 0.1 to about 20.

10. Process according to claim 9 wherein the alkyl aluminum chloride to the acetylacetonate mole ratio is in the range between from about 0.5 to about 100.

* * * * *